(12) United States Patent
Hildesley et al.

(10) Patent No.: US 12,201,546 B2
(45) Date of Patent: Jan. 21, 2025

(54) ARMPIT SUPPORT

(71) Applicant: LIFBAK LIMITED, Auckland (NZ)

(72) Inventors: Mark Appleton Hildesley, Auckland (NZ); Cynthia J. Baker, Auckland (NZ)

(73) Assignee: Lifbak Limited, Aukland (NZ)

( * ) Notice: Subject to any disclaimer, the term of this patent is extended or adjusted under 35 U.S.C. 154(b) by 797 days.

(21) Appl. No.: 17/312,108

(22) PCT Filed: Dec. 9, 2019

(86) PCT No.: PCT/IB2019/060544
§ 371 (c)(1),
(2) Date: Jun. 9, 2021

(87) PCT Pub. No.: WO2020/128709
PCT Pub. Date: Jun. 25, 2020

(65) Prior Publication Data
US 2022/0023088 A1  Jan. 27, 2022

(30) Foreign Application Priority Data

Dec. 21, 2018 (NZ) .................................. 749606

(51) Int. Cl.
*A61F 5/37* (2006.01)
(52) U.S. Cl.
CPC .................. *A61F 5/3753* (2013.01)
(58) Field of Classification Search
CPC .. A61F 5/3753; A61F 5/02; A61F 5/30; A61F 5/026; A61F 5/01; A61F 5/024; A61F 5/028; A61F 5/03; A61F 5/013; A61F 2005/0158; A61F 5/37; A61H 3/02; A61H 2201/1638; A63B 21/4009
See application file for complete search history.

(56) References Cited

U.S. PATENT DOCUMENTS

| | | | |
|---|---|---|---|
| 5,462,518 A | * | 10/1995 | Hatley .............. A63B 21/4009 482/124 |
| 5,725,005 A | | 3/1998 | Yamasaki et al. |
| 9,375,379 B1 | | 6/2016 | Morier |
| 2014/0096804 A1 | | 4/2014 | Keck |
| 2016/0278962 A1 | | 9/2016 | Zhang |

FOREIGN PATENT DOCUMENTS

| | | |
|---|---|---|
| CA | 2886860 A1 | 10/2016 |
| DE | 19850993 A1 | 4/1999 |
| WO | 2002045631 A1 | 6/2002 |
| WO | 2007027098 A1 | 3/2007 |
| WO | 2007095195 A2 | 8/2007 |
| WO | 2020128709 A1 | 6/2020 |

OTHER PUBLICATIONS

Australian Patent Office, International Search Report and Written Opinion for PCT/IB2019/060544 dated Feb. 27, 2020, 12 pages.

* cited by examiner

Primary Examiner — Ophelia A Hawthorne
(74) Attorney, Agent, or Firm — Edwin S. Flores; Daniel J. Chalker; Chalker Flores, LLP

(57) ABSTRACT

A support device configured to transfer load from a user's armpit to that user's hips or torso which includes an armpit support, wherein said armpit support includes a central section from which a first and second wing extend asymmetrically, such that the armpit support is configured to provide enough resistance to cause and hold a slight shoulder extension.

17 Claims, 4 Drawing Sheets

ARMPIT SUPPORT

CROSS-REFERENCE TO RELATED APPLICATIONS

This application is a National Stage of International Application No. PCT/IB2019/060544, filed Dec. 9, 2019, claiming the priority of New Zealand Application No. 749606, filed Dec. 21, 2018. The contents of each of which are incorporated by reference in their entirety.

TECHNICAL FIELD

The present device is an armpit support for use with a support device that transfers load from the armpit to the user's hip/torso.

BACKGROUND ART

Underarm, or armpit support devices are part of many pieces of equipment, for example crutches and spinal support systems. These armpit supports engage with all or part of the armpit.

Originally armpit supports were simply rigid Y-shaped or T-shaped components, the end of a tree branch used as a crutch for example, these provided support but were often uncomfortable and as such they were wrapped with a variety of materials to improve the comfort. As more work was carried out and additional materials became available these T- or Y-shaped armpit supports were covered with foam to mitigate the discomfort, unfortunately these still compress the underlying structures of the axilla. This compression of the underlying structure of the axilla can result in a variety of undesirable effects, for example:

pressure of a crutch on the nerves in the axilla may cause temporary paralysis, mainly in the radial distribution and to a lesser extent in the ulnar; and upward pressure into the axilla against resistance causes forward flexion of the shoulder and activates the clavicular part of the pectoralis major, while causing the sternocostal portion to be inactive. This allows depression into the muscle from e.g. a crutch. It also activates the upper fibres of the trapezius, the anterior fibres of the deltoid and the biceps increasing muscle fatigue, increasing depression into the pectoralis major muscle, and increasing the possibility of undesirable compression of the structures and vessels housed within the axilla.

There is an increasing use of devices that engage with the armpit to assist with spinal, musculoskeletal and other physiological problem correction solutions, and these may use the same armpit supports that crutches use. The use of current armpit supports for corrective solutions often creates pain, discomfort or other detrimental effects. To mitigate any resulting pain or discomfort pain killers may be used, however, these pain killers are unlikely to mitigate other detrimental effects and any increase in the use of pain killers is generally seen as undesirable.

To mitigate the pain or discomfort some armpit supports include additional features such as 'nerve notches', a cut away section of the support that aimed to reduce compression of underlying nerves, have been used with varying degrees of success.

Many, if not all, of the current armpit supports compress the underlying structures of the axilla to an undesirable (they create pain/discomfort to a user or compress structures resulting in reduced blood flow or movement) extent.

Most if not all of the current armpit supports are symmetrical and as such maintain the shoulder joint in a neutral position or cause flexion (forward motion in the sagittal plane) which is often undesirable but allows for a single configuration of armpit support to be used on both the left and right sides.

Any discussion of the prior art throughout the specification is not an admission that such prior art is widely known or forms part of the common general knowledge in the field.

The present invention ameliorates one or more of the deficiencies in existing armpit or axilla supports used with devices that transfer load from a user's armpit to that user's torso/hip, or at least provides the consumer with a useful choice.

DISCLOSURE OF INVENTION

The present invention provides an armpit support that includes a central section from which a first and second wing extend asymmetrically, such that the armpit support is configured to provide enough resistance to cause and hold a slight shoulder extension which in part activates the sternocostal portion of the pectoralis major so that depression into the muscle is minimised or avoided. Preferably the armpit support is also configured to inactivate the upper fibres of the trapezius, the anterior fibres of the deltoid and the biceps, preventing depression into the lower border of the pectoralis major. It is highly preferred that the armpit support includes a contact surface wherein:

the central section includes a portion of the contact surface that is configured to engage with (contact) the user, either directly on the user's skin, or any intervening skin covering proximate the upper portion of the lateral chest wall;

the first wing includes a portion of the contact surface, a first wing surface, that is configured to engage with (contact) the user, either directly on the user's skin, or any intervening skin covering, proximate the posterior fold of the axilla formed by the lower border of teres major; and the second wing includes a portion of the contact surface, the second wing surface, that is configured to engage with (contact) the user, either directly on the user's skin, or any intervening skin covering, proximate the anterior fold of the axilla formed by the lower border of pectoralis major.

Preferably the slight shoulder extension is insufficient to cause strong activation of either the latissimus dorsi muscle or strong activation of the rhomboid muscle group, or both, which, if activated by moderate shoulder extension, would cause the arm to move backwards and behind the back i.e. in extension and adduction.

The present invention also provides a support device configured to transfer load from a user's armpit to that user's hips or torso which includes an armpit support, wherein said armpit support includes a central section from which a first and second wing extend asymmetrically, such that the armpit support is configured to provide enough resistance to cause and hold a slight shoulder extension.

It is highly preferred that the armpit support includes a contact surface wherein:

the central section includes a portion of the contact surface that is configured to engage with (contact) the user, either directly on the user's skin, or any intervening skin covering proximate the upper portion of the lateral chest wall;

the first wing includes a portion of the contact surface, a first wing surface, that is configured to engage with (contact) the user, either directly on the user's skin, or any intervening skin covering, proximate the posterior fold of the axilla formed by the lower border of teres major; and the second wing includes a portion of the contact surface, a second wing surface, that is configured to engage with (contact) the user, either directly on the user's skin, or any intervening skin covering, proximate the anterior fold of the axilla formed by the lower border of pectoralis major.

Preferably the slight shoulder extension causes a kinetic chain which has the effect of reducing compression of the structures housed within the axilla by activating the sternocostal portion of the pectoralis major so that depression into the muscle is minimised or avoided and inactivating the upper fibres of the trapezius, the anterior fibres of the deltoid and the biceps, preventing depression into the lower border of the pectoralis major, which forms the anterior fold of the axilla.

Preferably the slight shoulder extension is insufficient to cause strong activation of either the latissimus dorsi muscle or strong activation of the rhomboid muscle group.

Preferably each wing terminates in a wing tip that incorporates a wing vertex, where each wing vertex, when the support device is in use in a rest position, is an apex of the associated wing.

Preferably the support device includes a support arm associated with each armpit support and an engagement device, where said support arms are configured to transfer load from the associated armpit support to the engagement device and the engagement device is configured to transfer this load to the user's hips or torso. In an alternative preferred form the support device includes a support arm and an engagement device associated with each armpit support, where the support arm is configured to transfer load from the associated armpit support to the associated engagement device, and the engagement device is configured to transfer this load to a user's hip or torso.

Preferably the armpit support includes:
a primary peripheral edge and a secondary peripheral edge which are peripheral edges of the armpit support that co-terminate at the first wing vertex and the second wing vertex;
an alpha axis which is co-axial with a longitudinal axis of the associated support arm; and
the primary peripheral edge is concave;
where the central section includes a central base which is coterminous with the side of the armpit support from which the associated armpit support extends and the secondary peripheral edge.

Preferably the dimensions of the armpit support are A, B, C, D, E and F where:
A is a line segment perpendicular to the alpha axis that extends between a line segment parallel to the alpha axis extending from the first wing vertex and a line segment parallel to the alpha axis extending from the second wing vertex;
B is a line segment parallel to the alpha axis that extends between a line segment parallel to line segment A that extends from the first wing vertex and a line segment parallel to line segment A that extends from the second wing vertex;
C is the longest line segment parallel to the alpha axis that extends between line segment A and the secondary peripheral edge;

D is a line segment extending between a line segment parallel to the alpha axis extending from the first wing vertex and line segment C;
E is a line segment extending between a line segment parallel to the alpha axis extending from the second wing vertex and line segment C; and
F is a line segment parallel to the alpha axis that extends between the primary peripheral edge and the secondary peripheral edge that is co-axial with line segment C.

In one preferred form the dimensions of the armpit support are:
A is 155 mm+/−25 mm long; and
C is from 0.35 A to 0.45 A in length.
Preferably D is from 0.4 A to 0.5 A in length. Preferably E is from 0.5 A to 0.6 A in length. Preferably the length of B is in the range extending from 0% to 8% of C. Preferably F is in the range of 10 to 1.3 C.

In an alternative preferred form the dimensions of the armpit support are:
A is in the range of 80 mm to 130 mm.
Preferably the length of C is from 0.35 A and 0.45 A. Preferably D is from 0.4 A to 0.5 A in length. Preferably E is from 0.5 A to 0.6 A in length. Preferably the length of B is in the range extending from 0% to 8% of C. Preferably F is in the range of 10 to 1.3 C.

Preferably when the armpit support is in use and at a temperature in the range of 36° C. to 39° C., the second wing vertex (25) moves sufficiently to reduce the as made dimension ((C−B)+F) by up to 60 mm (due to the change in the modulus of the armpit support). Preferably in this temperature range the as made dimension ((C−B)+F) is reduced by between 0.01 mm and 50 mm. Preferably the as made dimension ((C−B)+F) is reduced by between 5 mm and 50 mm, or between 10 mm and 50 mm, or between 20 mm and 50 mm, or between 5 mm and 40 mm. Preferably the as made dimension ((C−B)+F) is reduced by between L and M, where L=1 mm to 45 mm, and M=30 mm to 60 mm providing L<M (all specific intermediate ranges are specifically disclosed and included as options).

Preferably the armpit support, when viewed in any cross-sectional view which passes through both the primary peripheral edge and the secondary peripheral edge which is located only in one of the following, the first wing, the second wing or the central section, shows the contact surface as a convex or flat line segment.

The present invention also provides an armpit support that includes any device as described below.

Definitions (these are Included for the Avoidance of Doubt)

Extension Extension, when referring to the action of a joint, is a movement that increases the angle between the two parts that the joint is connecting, in the case of the shoulder joint this is the upper limb moving backward in the sagittal plane.

Flexion Flexion, when referring to the action of a joint, is a movement that decreases the angle between the two parts that the joint is connecting, in the case of the shoulder joint this is the upper limb moving forwards in the sagittal plane.

Modulus In this specification the use of the plain word 'modulus' refers to the modulus of elasticity or Young's modulus.

Shoulder abduction this occurs when the arm moves away from the midline of the body.

Shoulder adduction this occurs when the arm moves towards the midline of the body.

The term 'as made' is, when the armpit support is a moulded item, the same as the term 'as moulded'. The term 'as made' in general terms is the original shape or form of the item after it has been manufactured ready for a customer to use.

BRIEF DESCRIPTION OF DRAWINGS

By way of example only, a preferred embodiment of the present invention is described in detail below with reference to the accompanying drawings, in which.

For clarity we will provide a definition of the axilla, as it is the axilla which is affected by the armpit support used. The axilla is a pyramidal space, its base the domed axillary fascia, its apex a small triangular interval between the outer border of the first rib, the clavicle and the scapula.

The medial wall of the axilla is formed by the upper four ribs, their intercostal muscles and by the upper part of the serratus anterior. The anterior wall of the axilla is formed by pectoralis minor and the clavipectoral fascia. All these structures are completely covered by pectoralis major, the lower border of which forms the anterior fold of the axilla.

The posterior wall of the axilla is formed by the subscapularis and latissimus dorsi muscle. The lateral wall is formed by the humerus, the corocobrachialis and the short head of the biceps. The posterior fold of the axilla is formed by the lower border of the teres major.

At the junction of the anterior and lateral walls of the axilla lie the axillary vessels (artery and vein) and the brachial plexus, which enter the axilla through the apex enclosed within the fibrous axillary sheath, itself a prolongation of the prevertebral layer of the deep cervical fascia.

The axillary artery is divided into 3 parts. The first and second parts are very deep, covered by the clavipectoral fascia and pectoralis minor. The third part is covered by pectoralis major above, but below is superficial.

The second part (behind pectoralis minor) is related to the cords of the brachial plexus (lateral. posterior and medial) as their names indicate. Within the axilla the cords of the plexus gradually alter their position relative to the axillary artery. Appearing from under cover of pectoralis minor the cords divide into nerves for the upper limb, along the third part of the artery.

First Mode for Carrying Out the Invention

Figure 1:
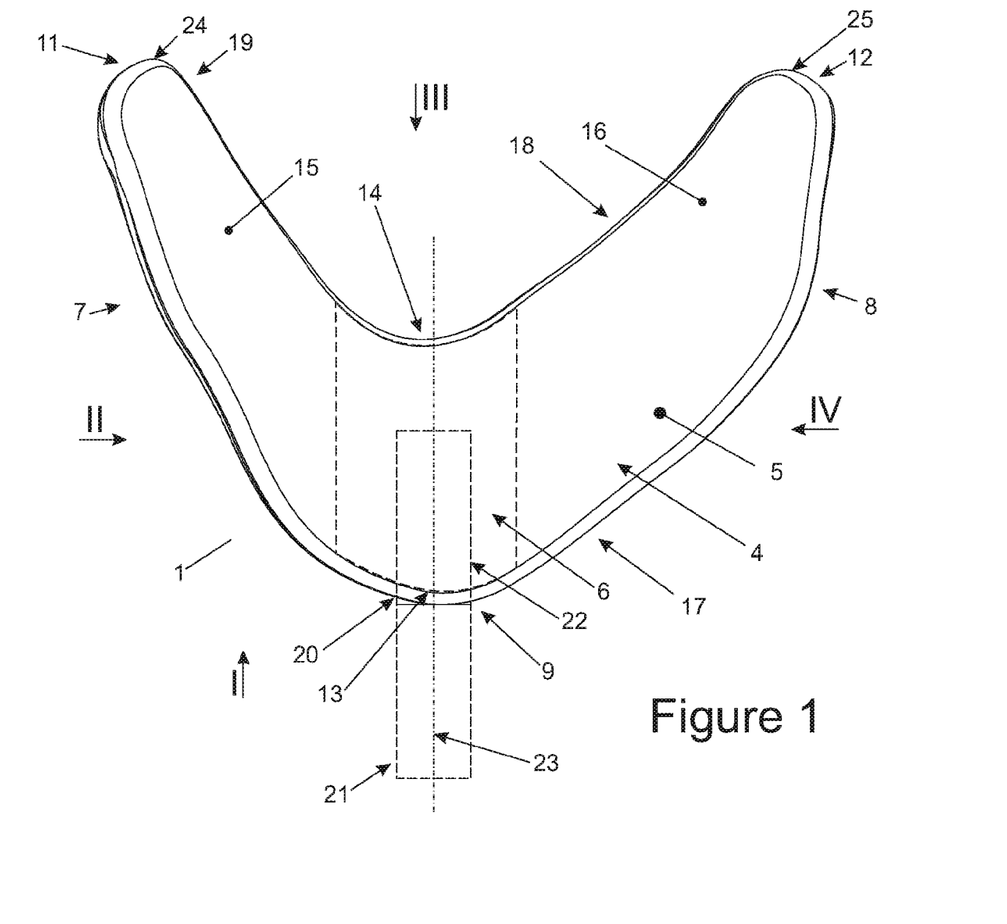
FIG. 1 is a view of a left-hand side armpit support with the contact side facing the viewer.

Referring to FIG. 1 an armpit support (1) for the left-hand side is shown in side view with the contact side (5) facing the viewer. The contact side (5) includes the contact surface (6) which is the exposed surface of the armpit support (1) that engages with (contacts) the user, either directly on the user's skin, or any intervening skin covering (bandages, clothing, etc.). Though the contact surface (6) is the primary contact surface that engages with a user other portions of the armpit support (1) may also contact the user.

The shape of the armpit support (1), in use, is intended to provide enough resistance to cause and hold a slight shoulder extension. The resultant kinetic chain (in this context a kinetic chain is a localised chain of interconnected structures—muscular, nervous and articular, interacting together) has the immediate effect of reducing compression of the structures housed within the axilla. It achieves this as follows: slight shoulder extension activates the sternocostal portion of the pectoralis major so that depression into the muscle is minimised or avoided. This same extension inactivates the upper fibres of the trapezius, the anterior fibres of the deltoid and the biceps, preventing depression into the lower border of the pectoralis major, which forms the anterior fold of the axilla.

A slight shoulder extension is insufficient to cause strong activation of either the latissimus dorsi muscle or strong activation of the rhomboid muscle group, or both, which, if activated by moderate shoulder extension, would cause the arm to move backwards and behind the back i.e. in extension and adduction. Extension with adduction or abduction is not considered a slight shoulder extension.

The armpit support (1), as shown in FIG. 1 looks like an asymmetric boomerang which includes a central section (6) from which two wings (7,8), a first wing (7) and a second wing (8), asymmetrically extend. The central section (6) further includes a central base (9) which is coterminous with a peripheral edge of the armpit support (1) that is, when the armpit support (1) is in use, furthest from the apex of the axilla. Each wing (7,8) terminates in a wing tip (11,12), a first wing tip (11) and a second wing tip (12), where each wing tip (11,12) is a curved edge of the associated wing (7,8) that is located furthest from the central base (9).

The central section (6), shown bounded by dashed lines in FIG. 1, is essentially a curved rectangle with asymmetrical curved sides that may not be parallel. The curved side coterminous with the central base (9), the first central side (13) is convex or linear. The opposite curved side of the curved rectangle, the second central side (14), is concave and coterminous with the peripheral edge of the armpit support (1) opposite the central base (9).

The central section (6) includes the portion of the contact surface (5) that, when the armpit support (1) is in use, engages with (contacts) the user, either directly on the user's skin, or any intervening skin covering (bandages, clothing, etc.) proximate the upper portion of the lateral chest wall.

The first wing (7) includes the portion of the contact surface (5), the first wing surface (15), that, when the armpit support (1) is in use, engages with (contacts) the user, either directly on the user's skin, or any intervening skin covering (bandages, clothing, etc.), proximate the posterior fold of the axilla formed by the lower border of teres major.

In use the second wing (8) includes the portion of the contact surface (5), the second wing surface (16), that, when the armpit support (1) is in use, engages with (contacts) the user, either directly on the user's skin, or any intervening skin covering (bandages, clothing, etc.), proximate the anterior fold of the axilla formed by the lower border of pectoralis major.

The peripheral edge of the armpit support (1) that is coterminous with the first central side (13) is the primary peripheral edge (17) and the peripheral edge of the armpit support that is coterminous with the second central side (14) is the secondary peripheral edge (18). Both the primary peripheral edge (17) and the secondary peripheral edge (18) are coterminous with the peripheral edges of the first wing tip (11) and the second wing tip (12), in combination these first and second peripheral edges (17,18) form the bounding peripheral edge (19) of the armpit support (1). It should be noted that in the armpit support (1) shown the peripheral edges (17,18,19) are all radiused for comfort, this may not be the case in some configurations which include flexible materials applied over a rigid skeleton.

Figure 2:
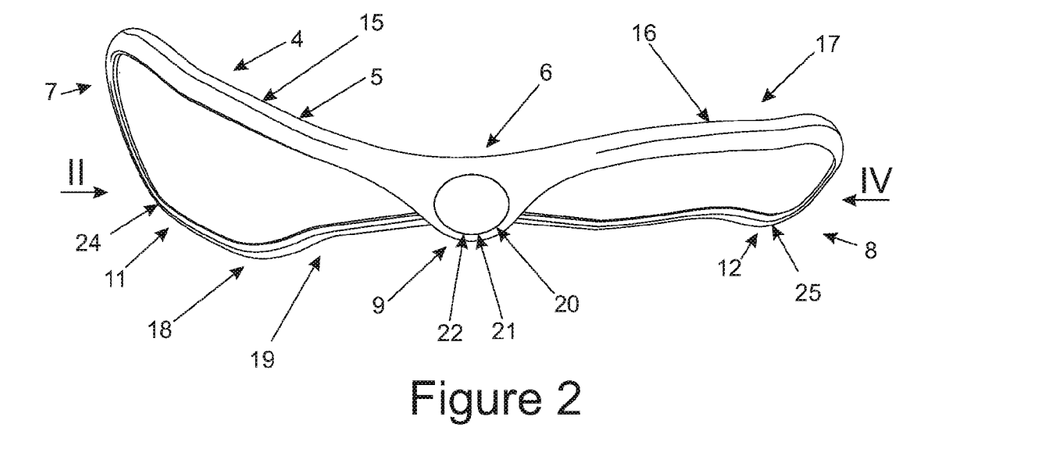
FIG. 2 is a view in the direction of arrow I, a view from the base of the armpit support.

Referring to FIG. 2 the wings (7,8) extend asymmetrically away from the central section (6), similar to the wings of a bird (gliding). In this view the central section (6) is concave in profile. In this view the central base (9) includes an engagement aperture (20) configured to accept a support member (21) (shown engaged with said engagement aperture (20) in dashed relief in FIG. 1). The support member (21) is part of a support device ((see FIGS. 8 and 9) that that transfers load to the hips/torso of a user. Where the support member (21) is releasably engaged with the armpit support (1) the engagement aperture (20) is the open end of an engagement tunnel (22) which has an alpha axis (23) which is the longitudinal axis of the engagement tunnel (22).

Referring to FIGS. 1 and 2 each wing tip (11,12) includes a wing vertex (24,25) where each wing vertex (24,25) is the portion of that wing tip (11,12) that is most distant from the central base (9). When the armpit support (1) is in use, and at the rest position, each wing vertex (24,25) forms the apex of the associated wing (7,8).

Figure 3:
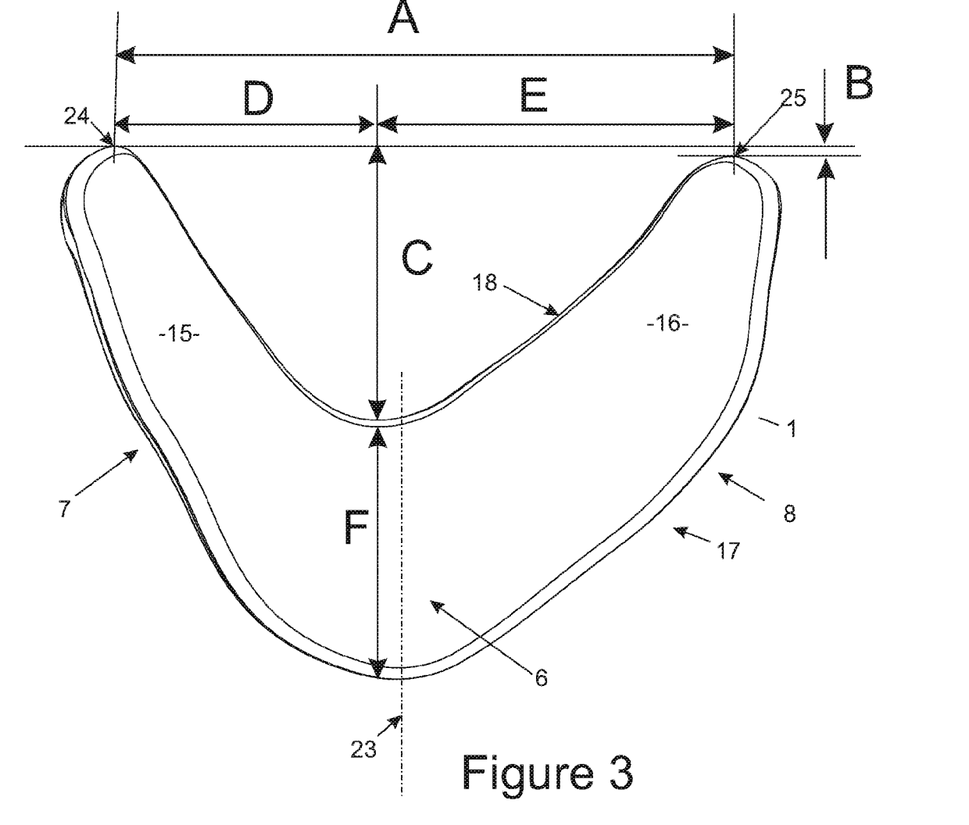
FIG. 3 is a view of a left-hand side armpit support with the contact side facing the viewer (the same as FIG. 1) with specific dimensions shown.

Referring to any of FIGS. 3 to 5 various features and dimensions will be discussed in more detail, where all dimensions are lengths along lines either parallel or perpendicular to the alpha axis (23), such that:

Referring to FIG. 3:
 A is a line segment perpendicular to the alpha axis (23) that extends between a line segment parallel to the alpha axis (23) extending from the first wing vertex (24) and a line segment parallel to the alpha axis (23) extending from the second wing vertex (25);
 B is a line segment parallel to the alpha axis (23) that extends between a line segment parallel to line segment A that extends from the first wing vertex (24) and a line segment parallel to line segment A that extends from the second wing vertex (25);
 C is the longest line segment parallel to the alpha axis (23) that extends between line segment A and the secondary peripheral edge (18);
 D is a line segment extending between a line segment parallel to the alpha axis (23) extending from the first wing vertex (24) and line segment C;
 E is a line segment extending between a line segment parallel to the alpha axis (23) extending from the second wing vertex (25) and line segment C; and
 F is a line segment parallel to the alpha axis (23) that extends between the primary peripheral edge (17) and the secondary peripheral edge (18) that is co-axial with line segment C.

Figure 4:
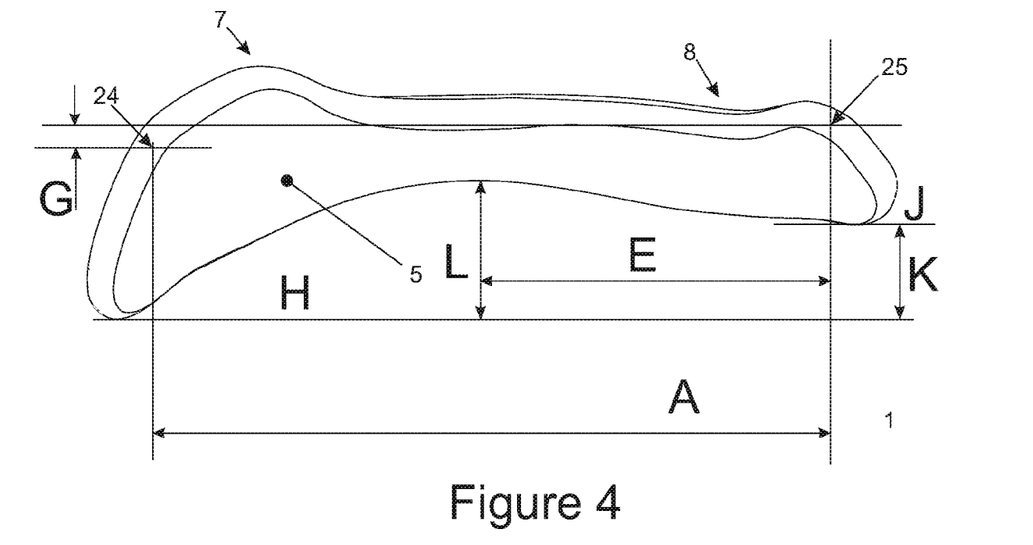
FIG. 4 is a view in the direction or arrow III with specific dimensions shown.
Figure 5:
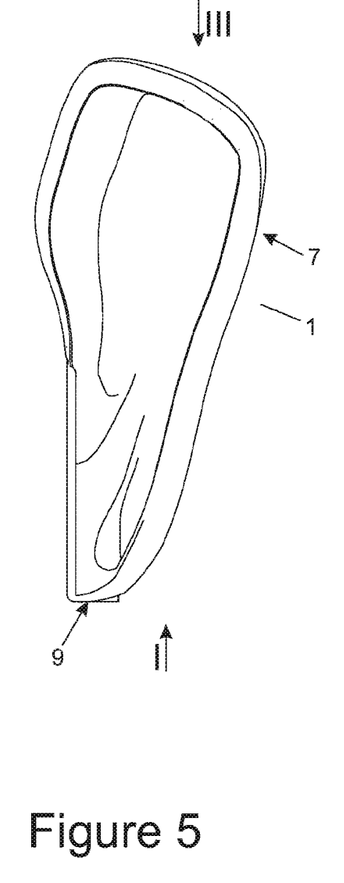
FIG. 5 is a view in the direction of arrow II, a view from the first end of the left-hand side armpit support looking towards the second end.
Figure 6:
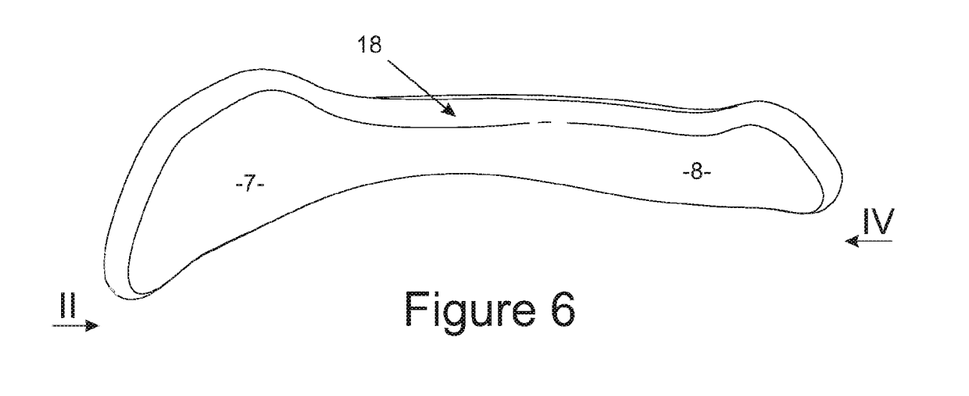
FIG. 6 is a view in the direction of arrow III.
Figure 7:
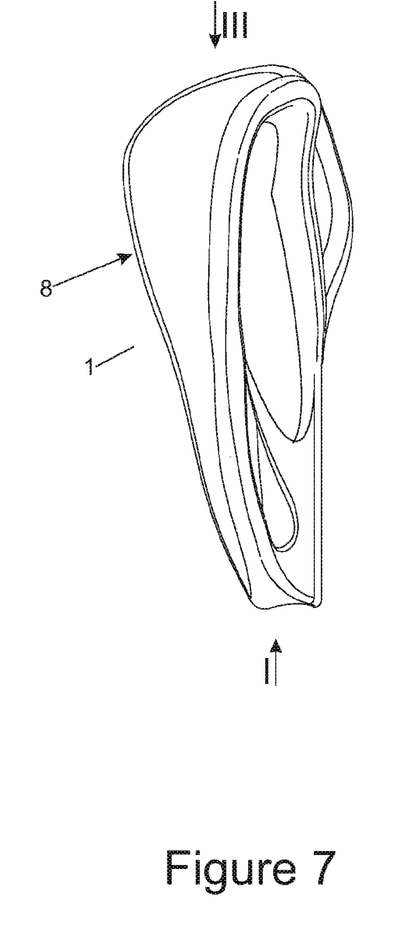
FIG. 7 is a view in the direction of arrow IV, a view from the second end of the left-hand side armpit support looking towards the first end.

Referring to FIG. 4:
 G is the distance between line segments that are parallel to line segment A that extends from each wing vertex (24,25);
 H is a line segment parallel to line segment A which contacts the first wing (7) tangentially;
 J is a line segment parallel to line segment A which contacts the second wing (8) tangentially;
 K is a line segment perpendicular to line A that extends between line segment H and line segment J; and
 L is the longest line segment perpendicular to line segment A that extends between line segment H and the contact surface (5).

For an armpit support (1) for use by a normal adult user the following dimensions and proportions have been found appropriate:
 A is 155 mm+/−25 mm long;
 C is from 0.35 A to 0.45 A in length; preferably
 D is from 0.4 A to 0.5 A in length; and preferably
 E is from 0.5 A to 0.6 A in length.
 Preferably the length of B is in the range extending from 0% to 8% of C.
 Preferably F is in the range of 10 to 1.3 C.
 Smaller armpit supports which have:
 The length of C is from 0.35 A and 0.45 A and preferably
 D is from 0.4 A to 0.5 A in length; and preferably
 E is from 0.5 A to 0.6 A in length; and preferably
 the length of B is in the range extending from 0% to 8% of C; and preferably
 F is in the range of 10 to 1.3 C; where
 A is in the range of 80 mm to 130 mm.

In use the second wing (8) of each armpit support (1) is frontmost, with the contact surface (6) proximate the user's torso. For clarity it should be noted that the right-hand side armpit support (1) is a mirror image of the left-hand side armpit support (1).

It was believed that a rigid armpit support (1) offered the best performance, accepting that some variants may allow a certain amount of flex. Still other configurations will include a resilient material such as a synthetic or natural polymer or foam, wool or similar natural materials, one or more known elastomeric materials to form, or lie under, the contact surface (5), a combination of one or more of these, or any material that can behave in a similar manner to further distribute the load across the armpit support (1). It has been determined that though a rigid arm support (1) provides good performance it does not necessarily provide the best performance.

It has been determined that if the modulus of the armpit support (1) reduces as the temperature increases, then this increases the contact surface area and improves comfort. Optimally this thermally induced reduction in the modulus is sufficient to increase the contact area whilst maintaining the slight shoulder extension and this occurs when the portion of the armpit support (1) in contact with a user is in the temperature range of 36° C. to 39° C. Once the temperature of the armpit support (1) falls below this range it returns to the original shape and rigidity, the speed with which the shape and rigidity returns is dependent on the materials of construction. Noting that to finally reach the original shape and rigidity the temperature of the armpit support (1) may need to be below 30° C., 25° C., 20° C. or less. Where the ambient temperature is above about 39° C. the armpit support (1) may return to the original shape as the temperature increases, though this may only start to occur when the temperature is in the range of 40° C. to 45° C.

It is likely that the armpit support (1) will be an elastomeric polymer or thermoplastic elastomer (TPE) formulated to have the required modulus reduction above 36° C. One suitable sub-group of TPE's is thermoplastic urethanes (TPU).

As the temperature increases into the range of 36° C. to 39° C. the armpit support (1) modulus falls to a level that allows the second wing vertex (25) to deform reducing the dimension ((C−B)+F) (see FIG. 3) by as much as 60 mm, preferably this reduction is in the in the range of 0.1 mm to 50 mm. Due to the complex shape of the armpit support (1) the deformation that causes the reduction in the dimension ((C−B)+F) involves movement away from the body of the user and increased curvature of the second wing surface (16) and possibly the central section (6). There may also be deformation of the first wing surface (15) which will reduce the dimension (C+F), however minimal deformation has been observed to date. Please note that due to the complex deformation caused by the reduction/change in modulus the dimensions A, D and E may also change.

For countries that experience high temperature (greater than around 40° C.) the modulus of the armpit support (1) will increase or decrease as it cools into the range of 36° C. to 39° C. such that the second wing vertex (25) deformation, from the as manufactured (as moulded, as made) dimension ((C−B)+F) (see FIG. 3) is a maximum of 60 mm, preferably in the range of 0.1 mm to 50 mm.

The engagement aperture (20) is shown as an oval in FIG. 2, this is representative only it may be any suitable cross-sectional shape, including but not limited to, crescent shaped, circular, rounded rectangle, rectangle, any regular or irregular polygon, stellated or not and any cross-section of a cone, cylinder, cube, dodecahedron, pyramid, sphere, ellipsoid, beam, or similar.

When the armpit support (1) is used in combination with a support member (20), then the armpit support (1) is able to rotate about the alpha axis (23), in some configurations this rotation may be limited to between 0 and 40 degrees, and preferably between 15 to 25 degrees. In use the angle adopted by the armpit support (1) is determined by the user and their armpit geometry, the distal end of the support member (20) is preferably configured to allow this to occur.

Figure 8:
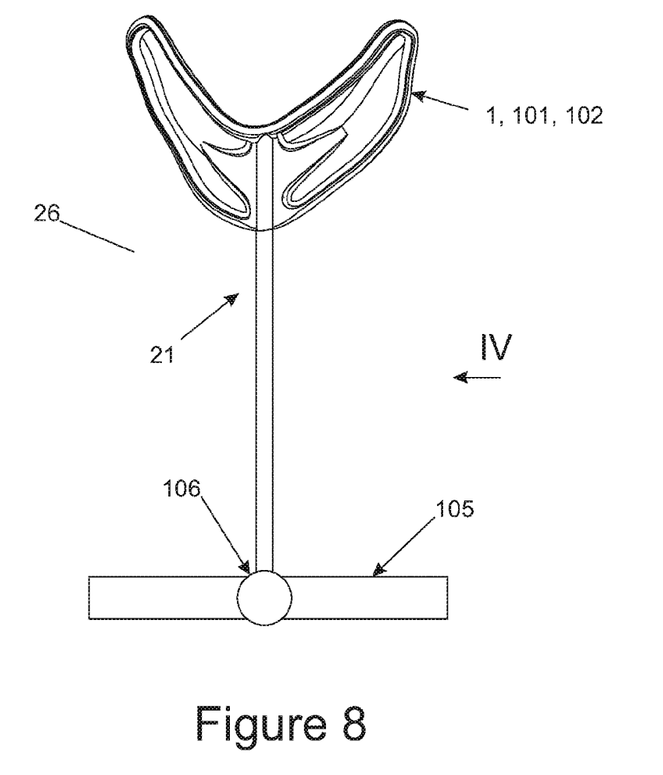
FIG. 8 is a side view of a support device incorporating the armpit support.
Figure 9:
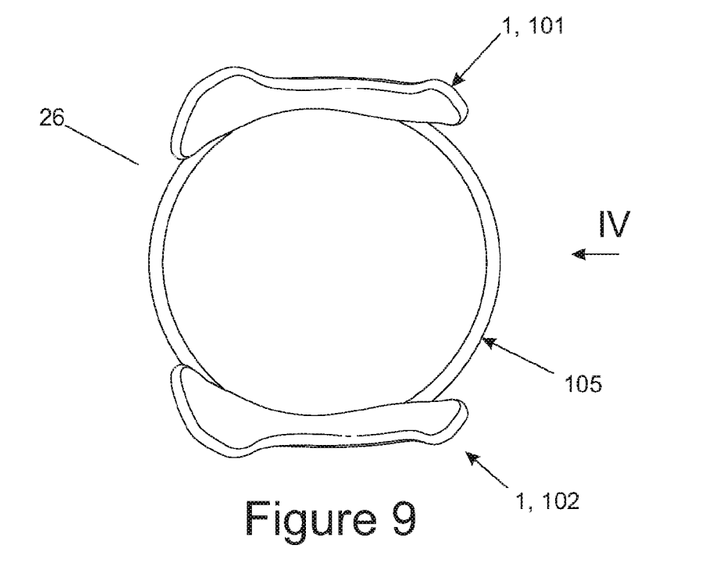
FIG. 9 is a plan view of a support device incorporating the armpit support.

Referring to FIGS. 8 and 9 a support device (26) including a first armpit support (101), a second armpit support (102) and an engagement device (105) is shown. In use the first armpit support (101) engages with a user's left hand armpit and the second armpit support (102) engages with a user's right hand armpit.

The engagement device (105) is connected to each armpit support (1,101,102) by a support member (21) via an engagement joint (106), these connections may be permanent, releasable or temporary. In use the engagement device (106) is engaged with a user (not shown) such that it can transfer the load from the user's armpit to the torso or hip(s) of the user. It has been found that transferring the load from a user's armpit to a user's hip(s) or torso is more comfortable than transferring that load to the back or thighs of a user.

Each engagement joint (106) may be a fixed point or a hinge joint which allows the connected armpit support (1,101,102) to move forwards and backwards in relation to the user.

The engagement device (105) is shown as a band which in use would surround the user's torso or hips.

In one variant (not shown) the engagement device (105) is two separated sub-units (not shown) each designed to engage with one of the user's hips, possibly joined together to prevent disengagement from the hips.

Referring to any of the drawings, the armpit support (1), when viewed in any cross-sectional view which passes through both the primary peripheral edge (17) and the secondary peripheral edge (18) which is located only in one of the following, the first wing (7), the second wing (8) or the central section (6), shows the contact surface (5) as a convex or flat line segment.

KEY

1. Armpit support;
4. Contact Side,
5. Contact surface of armpit support;
6. Central Section;
7. First wing;
8. Second wing;
9. Central Base;
11. First wing tip;
12. Second wing tip;
13. First Central side;
14. Second Central second side;
15. First wing surface;
16. Second wing surface;
17. Primary peripheral edge;
18. Secondary peripheral edge;
19. Bounding peripheral edge
20. Engagement aperture;
21. Support member;
22. Engagement tunnel;
23. Alpha axis;
24. First wing vertex;
25. Second wing vertex;
26. Support device;
101. First armpit support (LHS of user);
102. Second armpit support (RHS of user)
105. Engagement device;
106. Engagement joint;

The invention claimed is:

1. A support device configured to transfer load from a user's armpit to that user's hips or torso which includes an armpit support, characterised in that said armpit support includes a central section from which a first and second wing extend asymmetrically, each wing terminates in a wing tip that incorporates a wing vertex, where each wing vertex, when the support device is in use in a rest position, is an apex of each wing, respectively, such that the armpit support is configured to provide enough resistance to cause and hold a slight shoulder extension, wherein, the slight shoulder extension causes a kinetic chain which has the effect of reducing compression of structures housed within an axilla by activating a sternocostal portion of a pectoralis major so that depression into a muscle is minimised or avoided and inactivating upper fibres of a trapezius, anterior fibres of a deltoid and biceps, preventing depression into a lower border of the pectoralis major, which forms an anterior fold of the axilla, such that the slight shoulder extension is insufficient to cause strong activation of either a latissimus dorsi muscle or strong activation of a rhomboid muscle group;

wherein, the armpit support includes:
  a primary peripheral edge and a secondary peripheral edge which are peripheral edges of the armpit support that co-terminate at the first wing vertex and the second wing vertex;
  an alpha axis which is co-axial with a longitudinal axis of the associated support arm; and
  the primary peripheral edge is concave;
where the central section includes a central base which is coterminous with the side of the armpit support from which the armpit support extends and the secondary peripheral edge;
wherein, dimensions of the armpit support are A, B, C, D, E and F where:
  A is a line segment perpendicular to the alpha axis that extends between a line segment parallel to the alpha axis extending from the first wing vertex and a line segment parallel to the alpha axis extending from the second wing vertex;

B is a line segment parallel to the alpha axis that extends between a line segment parallel to line segment A that extends from the first wing vertex and a line segment parallel to line segment A that extends from the second wing vertex;

C is the longest line segment parallel to the alpha axis that extends between line segment A and the secondary peripheral edge;

D is a line segment extending between a line segment parallel to the alpha axis extending from the first wing vertex and line segment C;

E is a line segment extending between a line segment parallel to the alpha axis extending from the second wing vertex and line segment C; and F is a line segment parallel to the alpha axis that extends between the primary peripheral edge and the secondary peripheral edge that is co-axial with line segment C; and when the armpit support is in use and at a temperature in the range of 36° C. to 39° C., the second wing vertex is configured to move sufficiently to reduce the as made dimension ((C−B)+F) by up to 60 mm.

2. The support device as claimed in claim 1 wherein, A is in the range of 80 mm to 130 mm.

3. The support device as claimed in claim 2 wherein, C is from 0.35 A to 0.45 A.

4. The support device as claimed in claim 2 wherein, D is from 0.4 A to 0.5 A in length.

5. The support device as claimed in claim 2 wherein, E is from 0.5 A to 0.6 A in length.

6. The support device as claimed in claim 2 wherein, B is in the range extending from 0% to 8% of C.

7. The support device as claimed in claim 2 wherein, F is in the range of 1 C to 1.3 C.

8. The support device as claimed in claim 1 wherein, A is 155 mm+/−25 mm long; and C is from 0.35 A to 0.45 A in length.

9. The support device as claimed in claim 8 wherein, D is from 0.4 A to 0.5 A in length.

10. The support device as claimed in claim 8 wherein, E is from 0.5 A to 0.6 A in length.

11. The support device as claimed in claim 8 wherein, the length of B is in the range extending from 0% to 8% of C.

12. The support device as claimed in claim 8 wherein, F is in the range of 1 C to 1.3 C.

13. The support device as claimed in claim 1 wherein, the armpit support includes a contact surface wherein:
the central section includes a portion of the contact surface that is configured to engage with (contact) the user, either directly on the user's skin, or any intervening skin covering proximate an upper portion of a lateral chest wall;
the first wing includes a portion of the contact surface, a first wing surface, that is configured to engage with (contact) the user, either directly on the user's skin, or any intervening skin covering, proximate a posterior fold of the axilla formed by a lower border of teres major; and
the second wing includes a portion of the contact surface, a second wing surface, that is configured to engage with (contact) the user, either directly on the user's skin, or any intervening skin covering, proximate the anterior fold of the axilla formed by the lower border of pectoralis major.

14. The support device as claimed in claim 1 wherein, the support device includes a support arm for each armpit support and an engagement device, where said support arms are configured to transfer a load from the armpit support to the engagement device and the engagement device is configured to transfer this load to the user's hips or torso.

15. The support device as claimed in claim 1 wherein, the support device includes a support arm and an engagement device for each armpit support, where the support arm is configured to transfer a load from the armpit support to the engagement device, and the engagement device is configured to transfer this load to a user's hips or torso.

16. The support device as claimed in claim 1 wherein, the as made dimension ((C−B)+F) is reduced by 0.01 mm to 50 mm.

17. The support device as claimed in claim 1 wherein, when viewed in any cross-sectional view which passes through both the primary peripheral edge and the secondary peripheral edge which is located only in one of the following, the first wing, the second wing or the central section, shows the contact surface as a convex or flat line segment.

* * * * *